(12) United States Patent
Masumura

(10) Patent No.: US 9,494,422 B2
(45) Date of Patent: Nov. 15, 2016

(54) LIGHTING DEVICE FOR INSPECTION AND LIGHTING METHOD FOR INSPECTION

(71) Applicant: CCS Inc., Kyoto-shi, Kyoto (JP)

(72) Inventor: Shigeki Masumura, Kyoto (JP)

(73) Assignee: CCS Inc., Kyoto-shi (JP)

( * ) Notice: Subject to any disclaimer, the term of this patent is extended or adjusted under 35 U.S.C. 154(b) by 0 days.

(21) Appl. No.: 14/362,874

(22) PCT Filed: Nov. 27, 2012

(86) PCT No.: PCT/JP2012/080648
§ 371 (c)(1),
(2) Date: Jun. 4, 2014

(87) PCT Pub. No.: WO2013/084755
PCT Pub. Date: Jun. 13, 2013

(65) Prior Publication Data
US 2014/0355003 A1    Dec. 4, 2014

(30) Foreign Application Priority Data

Dec. 6, 2011    (JP) .................................. 2011-267321

(51) Int. Cl.
G01N 21/00    (2006.01)
G01B 11/30    (2006.01)
G01N 21/88    (2006.01)

(52) U.S. Cl.
CPC ........... *G01B 11/30* (2013.01); *G01N 21/8806* (2013.01); *G01N 2021/8809* (2013.01); *G01N 2021/8835* (2013.01); *G01N 2201/068* (2013.01)

(58) Field of Classification Search
USPC ........................ 356/237.1–237.6, 239.1–239.8
See application file for complete search history.

(56) References Cited

U.S. PATENT DOCUMENTS 5,737,074 A    4/1998    Haga et al.
6,690,469 B1   2/2004    Shibata et al.
(Continued)

FOREIGN PATENT DOCUMENTS

CN    1295242 A    5/2001
CN    1304822 A    7/2001
(Continued)

OTHER PUBLICATIONS

ISA Japanese Patent Office, International Search Report of PCT/JP2012/080648, WIPO, Feb. 19, 2013, 4 pages.
(Continued)

*Primary Examiner* — Tri T Ton
(74) *Attorney, Agent, or Firm* — Alleman Hall McCoy Russell & Tuttle LLP

(57) ABSTRACT

In order to make it possible for a difference between a defect and a normal part, such as contrast, to appear, a lighting device for inspection is provided with: a surface light source that emits inspection light; a lens that is provided on a light axis of the inspection light emitted from the surface light source, and between an inspection object and the surface light source; and a first diaphragm that is provided between the lens and the surface light source or the inspection object, wherein: the surface light source and the lens are set such that an image plane on which the surface light source is imaged is present near the inspection object; and the first diaphragm is set such that the central axis of an irradiation solid angle determined by a part of the inspection light is parallel to the light axis.

4 Claims, 14 Drawing Sheets

ENLARGED VIEW NEAR INSPECTION OBJECT

DIRECTIONAL DISTRIBUTION OF CENTRAL AXES OF SOLID ANGLES OF REFLECTED LIGHT

INSPECTION LIGHT IS IRRADIATED ONTO CONVEX SURFACE WITH FIRST DIAPHRAGM OUTSIDE FOCAL POINT

(56) References Cited

U.S. PATENT DOCUMENTS

| | | |
|---|---|---|
| 2002/0015148 A1 | 2/2002 | Tomomatsu |
| 2006/0268265 A1 | 11/2006 | Chuang et al. |
| 2009/0147247 A1 | 6/2009 | Endo et al. |
| 2010/0328765 A1* | 12/2010 | Dohi et al. .................... 359/385 |

FOREIGN PATENT DOCUMENTS

| | | |
|---|---|---|
| CN | 1489688 A | 4/2004 |
| CN | 2698097 Y | 5/2005 |
| CN | 201273878 Y | 7/2009 |
| CN | 201273879 Y | 7/2009 |
| CN | 201331494 Y | 10/2009 |
| JP | 2005148296 A | 6/2005 |
| JP | 2006046946 A | 2/2006 |
| JP | 2006258472 A | 9/2006 |
| JP | 2007133435 A | 5/2007 |
| JP | 2008076962 A | 4/2008 |
| JP | 2009019882 A | 1/2009 |
| JP | 2010261839 A | 11/2010 |
| JP | 2011028249 A | 2/2011 |
| WO | 03025656 A1 | 3/2003 |
| WO | 2010034433 A1 | 4/2010 |

OTHER PUBLICATIONS

European Patent Office, Extended European Search Report Issued in Application No. 12855609.9, Jun. 5, 2015, Germany, 8 pages.

Dai, T. et al., "New Optical Tutorial," Jun. 30, 1996, pp. 144-146, 5 pages. (See page 1, explanation of relevance).

* cited by examiner

—·—·— OBSERVATION SOLID ANGLE OF IMAGING DEVICE
············· IRRADIATION SOLID ANGLE ADJUSTED WITH FIRST DIAPHRAGM
——— SOLID ANGLE OF REFLECTED LIGHT
– – – MAXIMUM IRRADIATION SOLID ANGLE AND
MAXIMUM SOLID ANGLE OF REFLECTED LIGHT
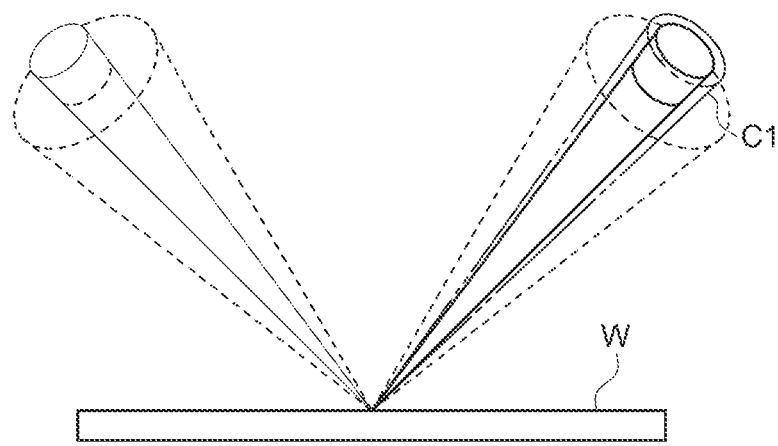
FIG. 5 (a) IN ABSENCE OF DEFECT
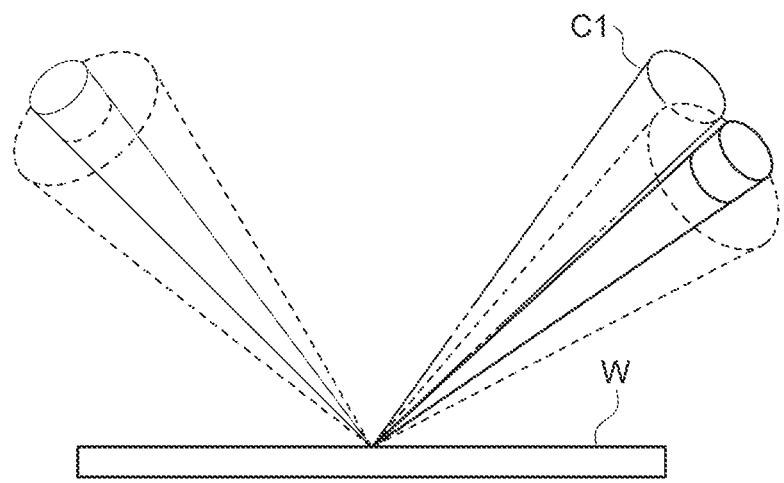
FIG. 5 (b) IN PRESENCE OF DEFECT

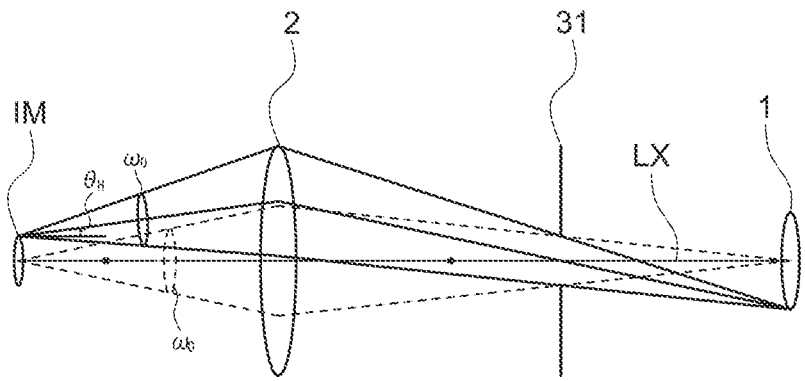
FIG. 10(a)  FIRST DIAPHRAGM IS OUTSIDE FOCAL POINT
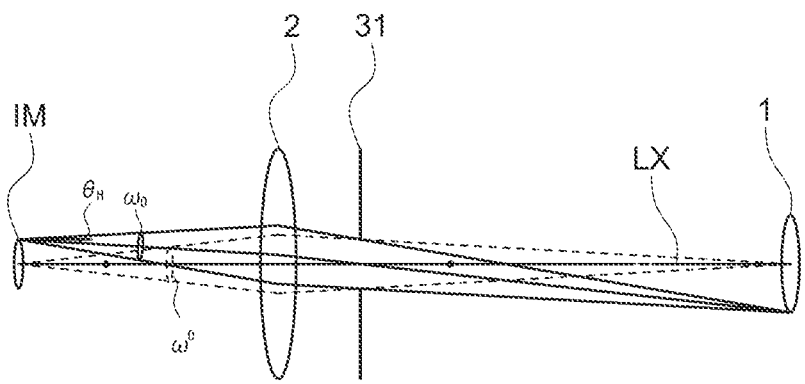
FIG. 10(b)  FIRST DIAPHRAGM IS INSIDE FOCAL POINT
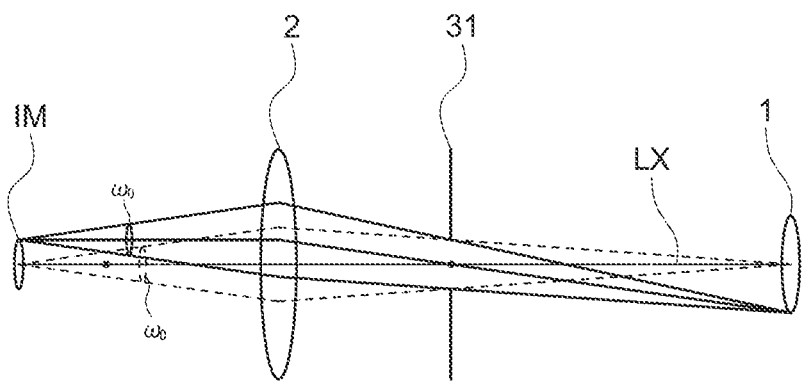
FIG. 10(c)  FIRST DIAPHRAGM IS AT FOCAL POINT ENLARGED VIEW NEAR IMAGE PLANE     DIRECTIONAL DISTRIBUTION OF CENTRAL AXES
                                    OF IRRADIATION SOLID ANGLES
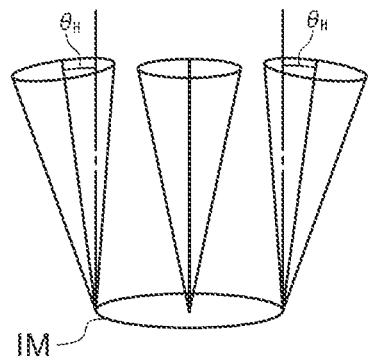 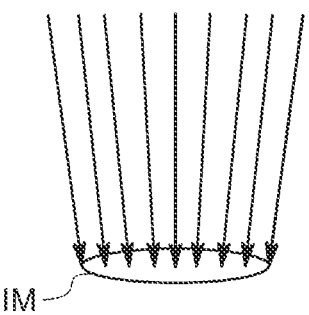
FIG. 11(a)   FIRST DIAPHRAGM IS OUTSIDE FOCAL POINT
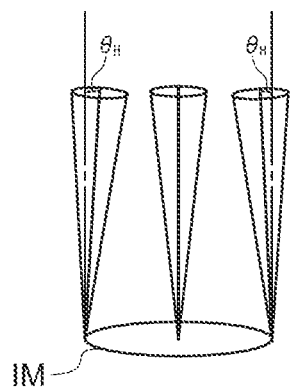 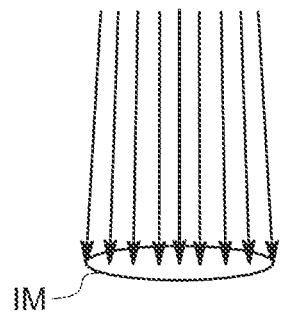
FIG. 11(b)   FIRST DIAPHRAGM IS INSIDE FOCAL POINT
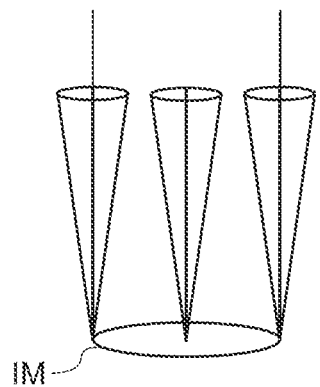 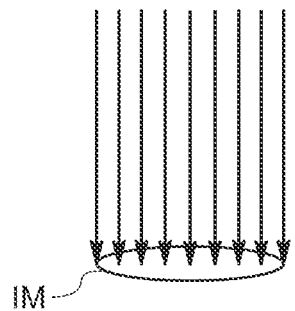
FIG. 11(c)   FIRST DIAPHRAGM IS AT FOCAL POINT ENLARGED VIEW NEAR INSPECTION OBJECT    DIRECTIONAL DISTRIBUTION OF CENTRAL AXES OF SOLID ANGLES OF REFLECTED LIGHT

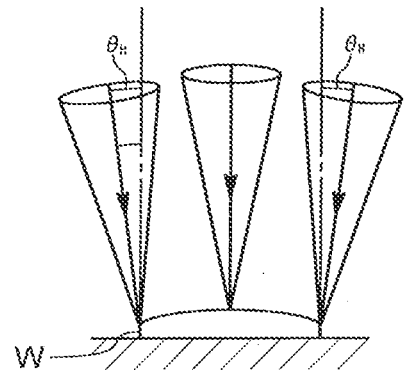 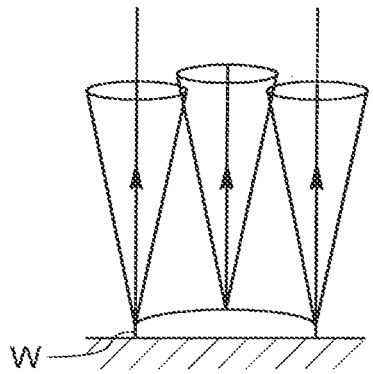

FIG. 12 (a)  INSPECTION LIGHT IS IRRADIATED ONTO CONVEX SURFACE WITH FIRST DIAPHRAGM OUTSIDE FOCAL POINT

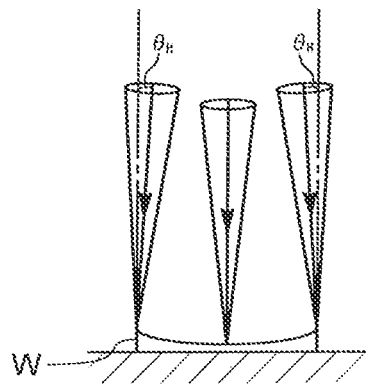 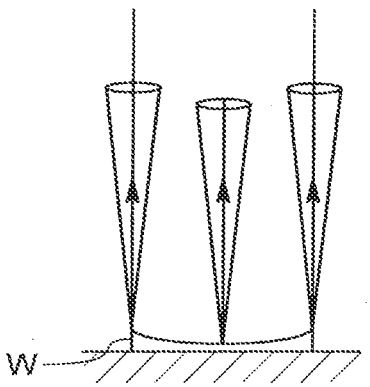

FIG. 12 (b)  INSPECTION LIGHT IS IRRADIATED ONTO CONCAVE SURFACE WITH FIRST DIAPHRAGM INSIDE FOCAL POINT

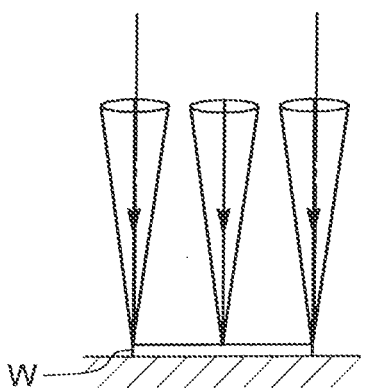 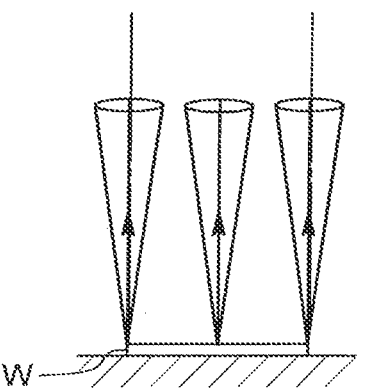

FIG. 12 (c)  INSPECTION LIGHT IS IRRADIATED ONTO FLAT SURFACE WITH FIRST DIAPHRAGM AT FOCAL POINT

LIGHTING DEVICE FOR INSPECTION AND LIGHTING METHOD FOR INSPECTION

TECHNICAL FIELD

The present invention relates to a lighting device for inspection and lighting method for inspection that are used in order to, for example, irradiate inspection light onto a product as an inspection object to inspect an appearance, flaw, defect, and the like of the product.

BACKGROUND ART

As an example of a lighting device for inspection used for purposes such as appearance inspection of products, as described in Patent Literature 1, a coaxial lighting device that makes an imaging direction coincide with a direction of lighting an inspection object can be cited. The coaxial lighting device is provided with: a light source that emits inspection light in a horizontal direction; and a half mirror that is provided at a tilt between the inspection object and an imaging device provided above the inspection object, and arranged so as to reflect the inspection light toward the inspection object as well as transmitting reflected light from the inspection object toward the imaging device.

Meanwhile, in recent years, making it possible to, from a captured image, detect feature points such as defects that are difficult to detect even when using a lighting device for inspection as described above has been demanded. More specifically, there are cases where inspection is difficult, such as a case where the shape of a product to be inspected is special or complicated, and therefore it is difficult to irradiate inspection light at sufficient intensity or light amount, a case where even if inspection light can be irradiated, the amount of reflected light from points other than a desired inspection point is too large, and a case where feature points such as defects are too small or even insensible, and therefore contrast is not easy to see.

For example, it is possible to, by using a diaphragm or the like to limit an irradiation range of inspection light only to an inspection object, reduce the amount of stray light including reflected light and scattered light from objects other than the inspection object to increase inspection accuracy. However, for example, in the case where the inspection object is small or even insensible, it is difficult to detect a change amount by which irradiated light is changed by feature points such as defects, and therefore the contrast between a defect and a normal part is more difficult to see.

Also, an inspection object may have a flat surface in some cases, or in other cases, it may have a slight convex or concave surface, and therefore one cause of unsuccessful defect detection is that tilt states of the central axes of irradiation solid angles at respective points on the inspection object are not appropriate for the inspection object. However, in the past, there has not been known a lighting device for inspection that can appropriately set tilt states of the central axes of irradiation solid angles at respective points on an inspection object, and the magnitudes of the irradiation solid angles to tilt states and values appropriate for the inspection object, respectively.

Accordingly, there has been demanded a lighting device for inspection that makes it possible to, through machine vision, detect defects even for a product of which a difference between a defect and a normal part does not easily appear in a captured image as described above.

CITATION LIST

Patent Literature

Patent Literature 1: JP-A2010-261839

SUMMARY OF INVENTION

Technical Problem

The present invention is made in consideration of the above-described problem, and intended to provide a lighting device for inspection and lighting method for inspection that, for example, even in the case where lighting conditions are severe, or a feature point such as a defect is very small or even insensible, make it possible to make differences such as contrast appear on the basis of a change amount of inspection light at the feature point. More specifically, the present invention is intended to provide a lighting device for inspection and lighting method for inspection that make it possible to make most emitted inspection light reach an inspection object, and also adjust tilt states of the central axes of irradiation solid angles of the inspection light at respective points on the inspection object, and the magnitudes of the irradiation solid angles to perform inspection appropriate for the shape and characteristics of the inspection object.

Solution to Problem

That is, the lighting device for inspection of the present invention is provided with: a surface light source that emits inspection light; a lens that is provided on a light axis of the inspection light emitted from the surface light source, and between an inspection object and the surface light source; and a first diaphragm that is provided between the surface light source and the lens, or between the lens and the inspection object, wherein: positions of the surface light source and the lens with respect to the inspection object are set such that an image plane on which the surface light source is imaged is present near the inspection object; and a position of the first diaphragm with respect to the lens is set such that a central axis of an irradiation solid angle determined by a part of the inspection light, which is incident on an outer edge part of the image plane, is parallel to the light axis, or is displaced from the light axis and tilted by a predetermined amount.

Also, the lighting method for inspection of the present invention is a lighting method for inspection used for a lighting device for inspection provided with: a surface light source that emits inspection light; a lens that is provided on a light axis of the inspection light emitted from the surface light source, and between an inspection object and the surface light source; and a first diaphragm that is provided between the surface light source and the lens, or between the lens and the inspection object. The lighting method for inspection includes: an imaging position setting step of setting positions of the surface light source and the lens with respect to the inspection object such that an image plane on which the surface light source is imaged is set near the inspection object; and an irradiation solid angle tilt adjusting step of setting a position of the first diaphragm with respect to the lens such that a central axis of an irradiation solid angle determined by a part of the inspection light, which is incident on an outer edge part of the image plane, is parallel to the light axis, or is displaced from the light axis and tilted by a predetermined amount.

If so, the positions of the surface light source and the lens with respect to the inspection object are set such that the image plane on which the surface light source is imaged is present near the inspection object, and therefore the inspection light emitted from the surface light source can be irradiated only onto the inspection object with being hardly blocked. Further, the position of the first diaphragm with respect to the lens is arranged such that the central axis of the irradiation solid angle determined by the part of the inspection light, which is incident on the outer edge part of the image plane, is parallel to the light axis, or is displaced from the light axis and tilted by the predetermined amount, and therefore central axes of irradiation solid angles of the inspection light irradiated onto respective points of the inspection object can be brought into tilt states appropriate for detecting feature points such as defects. Further, the first diaphragm is arranged with the image plane being present near the inspection object, and therefore the magnitudes of the irradiation solid angles can be changed with a range where the inspection light is irradiated remaining the same as the size of the image plane with no change.

That is, the irradiation range of the inspection light, and the irradiation solid angles can be independently adjusted, so that the irradiation range of the inspection light can be set appropriately for, for example, feature points occurring in the inspection point, such as defects, or the size or shape characteristics of a desired inspection site, and also the irradiation solid angles of the inspection light can be adjusted to be small. Accordingly, solid angles of reflected light produced by reflection of the inspection light at the inspection object can also be decreased, and even in the case where a reflection direction of the reflected light is changed only slightly by feature points such as defects, most of the solid angles of the reflected light deviate from corresponding observation solid angles of an imaging device because the solid angles of the reflected light are small, and thus the feature points such as defects are easily detected as contrast.

Alternatively, by adjusting an inclusion relation between the irradiation solid angle and corresponding observation solid angles, only feature points of which feature amounts are at a certain level or more can be selectively extracted to prevent the other feature points from being detected.

For example, in the case where the inspection object has a convex surface, to make directions of the central axes of solid angles of reflected light at respective points on the convex surface of the inspection object substantially parallel to the light axis to make it easy to perform defect inspection, it is only necessary that the first diaphragm is arranged outside a focal point of the lens such that the central axis of the irradiation solid angle is tilted from an outer edge side toward a center side of the image plane.

For example, in the case where the inspection object has a concave surface, to make directions of the central axes of solid angles of reflected light returned from respective points on the concave surface respectively uniformly parallel to make it easy to detect defects, it is only necessary that the first diaphragm is arranged inside a focal point of the lens such that the central axis of the irradiation solid angle is tilted from a center side toward an outer edge side of the image plane.

For example, in the case where the inspection object has a flat surface, to make directions of the central axes of solid angles of reflected light from the flat surface uniform to make it easy to perform defect inspection or the like, it is only necessary that the first diaphragm is arranged at a focal point of the lens such that the central axis of the irradiation solid angle is parallel to the light axis.

To adjust a tilt distribution of the irradiation solid angles and the magnitudes of the irradiation solid angles appropriately for inspecting the inspection object, it is only necessary that the position of the first diaphragm is set on the basis of an angle formed between the central axis of the irradiation solid angle and the light axis, and a magnification ratio on the image plane on which the surface light source is imaged through the lens.

In addition, the above operations make it possible to adjust tilts of the irradiation solid angles so as to uniform a captured image appropriately for characteristics of an observation optical system used for observation.

To make it possible to appropriately adjust the irradiation range of the inspection light irradiated onto the inspection object, or the maximum irradiation solid angle to make it easy to make the adjustment appropriately for each inspection object with the first diaphragm, it is only necessary that a second diaphragm that adjusts an emission area of the inspection light emitted from the surface light source is provided near the light source.

To prevent stray light, which is light such as reflected light from a part of the inspection object not relevant to the inspection, to make it easier to adjust the irradiation range of the inspection light onto the inspection object, or the solid angles of the reflected light to a size or magnitudes appropriate for the inspection, it is only necessary that a third diaphragm is further provided between the inspection object and an imaging device that images the inspection object.

To make it possible to obtain desired contrast on the basis of the solid angles of the reflected light, and changes in reflection direction, and more precisely adjust the observation solid angles at which the contrast is observed, it is only necessary that a fourth diaphragm is further provided between the third diaphragm and the imaging device.

To make it possible to simultaneously adjust both of the irradiation solid angles and the observation solid angles with the third diaphragm, it is only necessary that the lighting device for inspection is further provided with a half mirror that reflects the inspection light emitted from the light source toward the inspection object and is arranged so as to transmit reflected light from the inspection object, wherein the third diaphragm is arranged in a part where an irradiation light path that is a light path along which the inspection light reaches the inspection object from the light source, and a reflection light path including at least a light path from the inspection object to the half mirror overlap each other.

Advantageous Effects of Invention

As described, according to the lighting device for inspection and lighting method for inspection of the present invention, the magnitudes of the irradiation solid angles of the inspection light irradiated onto the inspection object, and the tilts of the central axes of the irradiation solid angles with respect to the light axis can be appropriately adjusted with the first diaphragm, and the solid angles of the reflected light from the inspection object can also be appropriately changed. Accordingly, even for feature points such as very small defects, which are ones that could not have easily appeared as contrast in a captured image previously, contrast can be made to appear because an inclusion relation between the solid angles of the reflected light and corresponding observation solid angles of the imaging device or the like can be optimized. Further, independently from the control of the irradiation solid angles, the irradiation range of the inspection light irradiated onto the inspection object can be appropriately set. That is, the irradiation range of the inspection light, and the irradiation solid angles at respective points in the irradiation range can be independently controlled, and therefore even an object or defect, which has been difficult to inspect previously, can be easily detected through machine vision or the like.

BRIEF DESCRIPTION OF DRAWINGS

FIGS. 5(a) and 5(b) are schematic diagrams illustrating a principle of the first embodiment that a solid angle of reflected light can be adjusted, and thereby a defect can be easily found.

FIG. 10(a)-(c) are schematic diagrams explaining a change in tilt of an irradiation solid angle due to a change in position of the first diaphragm of the lighting device for inspection in the second embodiment.

FIG. 11(a)-(c) are schematic diagrams illustrating a tilt distribution of irradiation solid angles depending on a position of the first diaphragm of the lighting device for inspection in the second embodiment.

FIG. 12(a)-(c) are schematic diagrams illustrating an example of a way to utilize the lighting device for inspection in the second embodiment.

REFERENCE CHARACTER LIST

Figure 1:
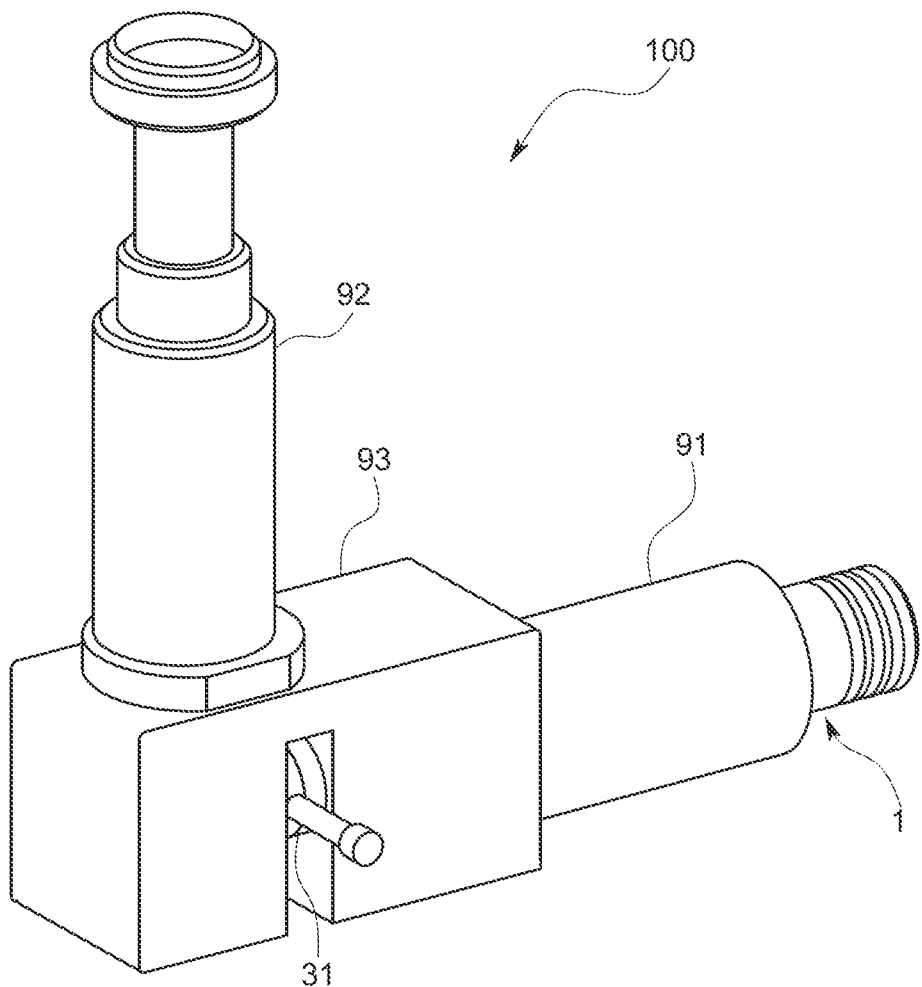
FIG. 1 is a schematic perspective view illustrating an appearance of a lighting device for inspection in a first embodiment of the present invention.

100 Lighting device for inspection
1 Light source
2 Lens
31 First diaphragm
32 Second diaphragm
33 Third diaphragm
34 Fourth diaphragm
4 Half mirror
C Imaging device
W Inspection object

DESCRIPTION OF EMBODIMENTS

A first embodiment of the present invention is described.

A lighting device for inspection 100 of the first embodiment is a so-called coaxial lighting device in which a direction of imaging an inspection object W with an imaging device C and a direction of lighting the inspection object W coincide with each other, and used to make defects of the inspection object W appear as contrast in an image captured by the imaging device C. Note that feature points such as the defects of the inspection object W are ones including a wide variety of undesired features such as surface flaws, undesired external form, and the presence or absence of pores, and other features and/or quantities.

Figure 2:
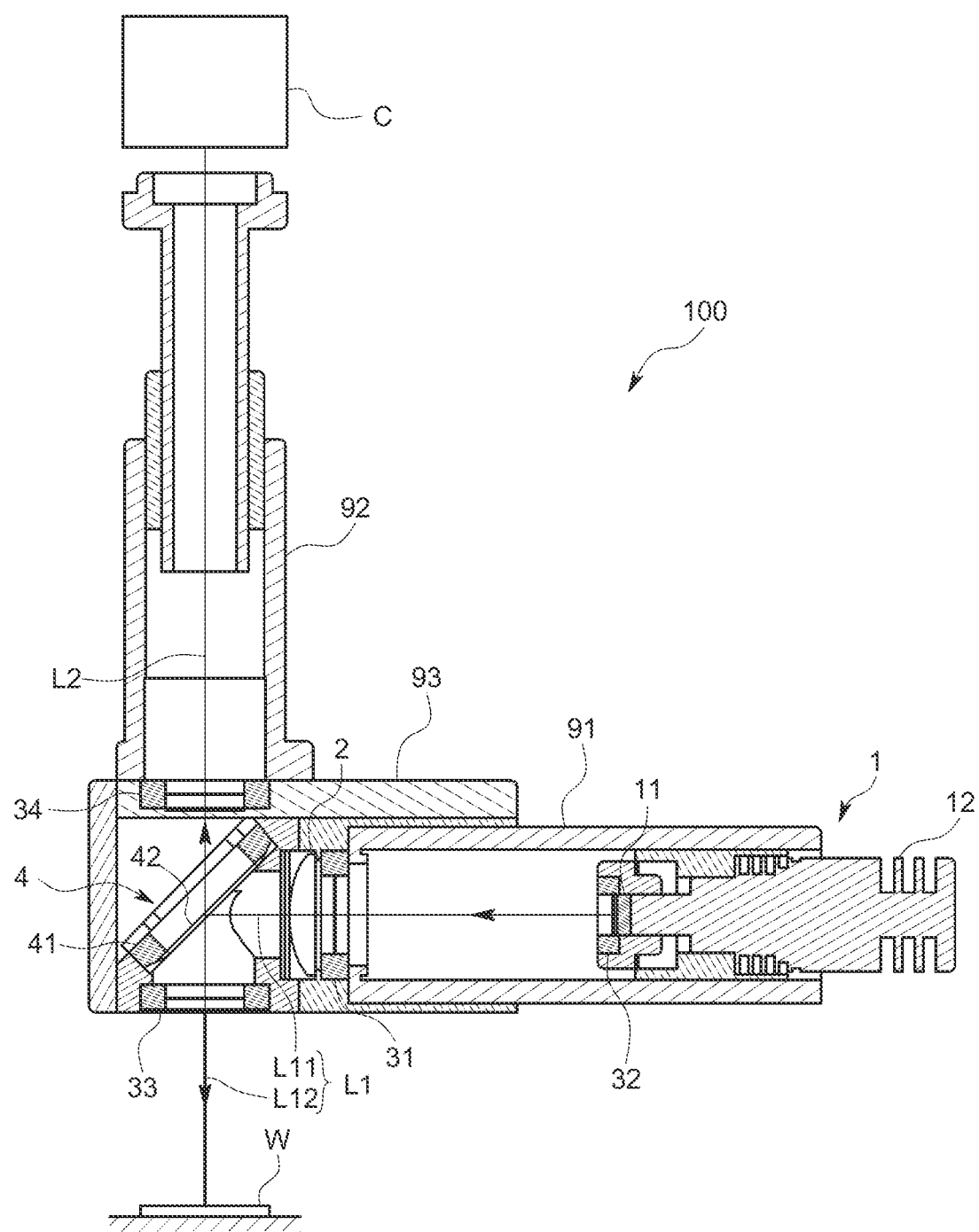
FIG. 2 is a schematic cross-sectional view of the lighting device for inspection in the first embodiment.

The lighting device for inspection 100 is, as illustrated in a perspective view of FIG. 1 and a cross-sectional view of FIG. 2, one that has a substantially L-shaped casing, inside which an irradiation light path L1 along which inspection light is irradiated from a light source 1 onto the inspection object W, and a reflection light path L2 along which reflected light from the inspection object W reaches the imaging device C are formed. More specifically, a first tubular body 91 extending in a horizontal direction, and a second tubular body 92 extending in a vertical direction are respectively connected to a box body 93, and on an upper surface opening side of the second tubular body 92 extending in the vertical direction, the imaging device C is attached, whereas the inspection object W is placed on a lower surface opening side of the box body 93.

Figure 3:
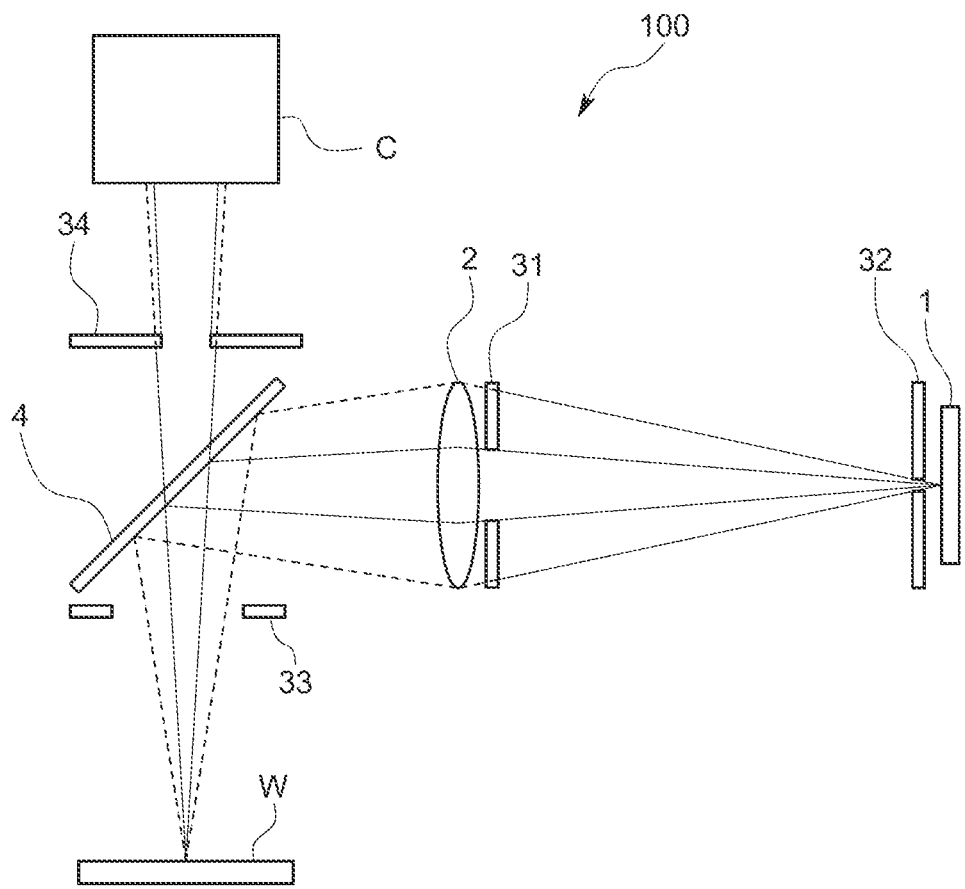
FIG. 3 is a schematic diagram illustrating a simplified light path in the lighting device for inspection in the first embodiment.

As illustrated in the cross-sectional view of FIG. 2, and in a simplified light path diagram of FIG. 3, the irradiation light path L1 is formed in an L-shape, and consists of a first light path L11 along which the inspection light travels in the horizontal direction, and a second light path L12 along which the inspection light is reflected and consequently travels downward.

In the first light path L11, the light source 1 that emits the inspection light, a second diaphragm 32 that is provided near the light source 1, a lens 2 that condenses the inspection light emitted from the light source 1, a first diaphragm 31 that is provided near a light incidence side of the lens 2, a half mirror 4 that is provided at a tilt with respect to the reflection light path L2 and the irradiation light path L1 so as to reflect the inspection light downward are arranged sequentially in a traveling direction of the inspection light. Further, in the second light path L12, a third diaphragm 33 through which the inspection light reflected by the half mirror 4 passes is provided. The inspection light having passed through the third diaphragm 33 from the inside of the box body 93 is irradiated onto the inspection object W.

On the other hand, in the reflection light path L2, the above-described third diaphragm 33, the half mirror 4, and a fourth diaphragm 34 attached on an upper surface of the box body 93 are provided before the imaging device C sequentially in a traveling direction of the reflected light reflected from the inspection object W. That is, the half mirror 4 and the third diaphragm 33 are arranged in a part where the irradiation light path L1 and the reflection light path L2 overlap each other. Note that the above-described first, second, third, and fourth diaphragms 31, 32, 33, and 34 are respectively variable diaphragms, and therefore stops of the diaphragms can be appropriately changed. Alternatively, depending on a use mode, the diaphragms 31, 32, 33, and 34 may be fixed diaphragms of which stops are fixed.

In the following, the arrangement and configuration of each of the members are described in details.

The light source 1 is a surface light source of which a light emitting surface 11 is formed of, for example, chip-type light-emitting diodes (LEDs), or the like, and radiator fins 12 for heat radiation are protruded outward. Also, as illustrated in the cross-sectional view of FIG. 2, the surface light source 1 is fitted into the first tubular body 91 movably forward and backward in an axial direction, and adapted to be able to adjust an irradiation start position of the inspection light. That is, by changing a positional relationship among the surface light source 1, the lens 2, and the inspection object W independently from after-mentioned control of an irradiation solid angle by the first diaphragm 31, an irradiation range of the inspection light on the inspection object W can be controlled.

The second diaphragm 32 is provided near the light emitting surface 11 of the surface light source 1, and by adjusting the stop thereof, an irradiation area of the inspection light from the surface light source 1 can be changed to change the irradiation range of the inspection light on the inspection object W.

The lens 2 is fitted into a lateral surface opening part of the box body 93, and arranged such that an image plane, which is present at a position at which the light source is imaged, is positioned near a surface of the inspection object W.

Figure 4:
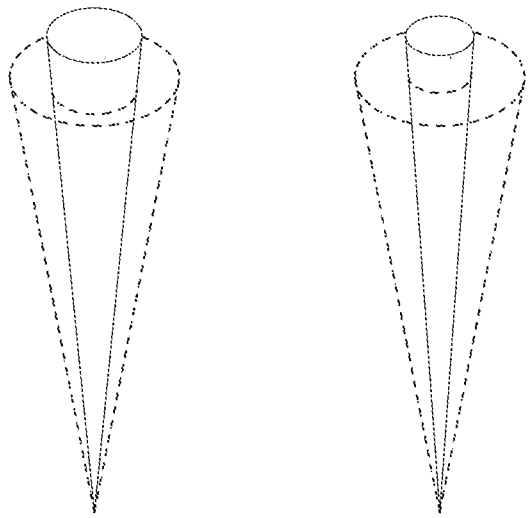
FIGS. 4(a) and 4(b) are schematic diagrams illustrating an example where an irradiation solid angle is changed with a first diaphragm of the lighting device for inspection in the first embodiment.

The first diaphragm 31 is provided on the light incidence side of the lens 2, and is intended to uniformly adjust irradiation solid angles of the inspection light condensed by the lens 2 at respective points within the irradiation range on the surface of the inspection object W. That is, by changing the stop of the first diaphragm, as illustrated in the schematic diagrams of FIGS. 4(a) and 4(b), the inspection light can be irradiated onto the inspection object W at any irradiation solid angle as long as the irradiation solid angle is smaller than a maximum irradiation solid angle determined by an aperture diameter of the lens 2.

The half mirror 4 is a circular-shaped thin one supported by a substantially square-shaped frame body 41. By using such a half mirror 4, a part of the half mirror 4 where the reflection or transmission takes place can be formed thin, and therefore an imaging error due to very small refraction or the like occurring when the reflected light from the inspection object W transmits through the half mirror 4 can be minimized.

The third diaphragm 33 is one that is fitted into a lower surface opening part of the box body 93, and is arranged between the half mirror 4 and the inspection object W. The third diaphragm 33 enables the irradiation solid angles determined by the first diaphragm 31 to be more finely adjusted. In addition, the third diaphragm 33 can also prevent stray light, which is produced when the inspection light having passed through the third diaphragm 33 is reflected by the inspection object W to become the reflected light, from entering the lighting device for inspection. Further, this diaphragm enables each of the irradiation solid angles and a corresponding observation solid angle to be made coaxially equal in magnitude to each other, and therefore sensitivity characteristics and an intensity profile of observation light, which is observed by the imaging device C, at the time of converting tilt variations of the reflected light into intensity information of the observation light can be changed.

The fourth diaphragm 34 is fitted into an upper surface opening part of the box body 93, and is arranged between the half mirror 4 and the imaging device C. The fourth diaphragm 34 is one that is intended to further adjust observation solid angles at which the reflected light incident on the imaging device C is observed. Also, the second tubular body 92 is telescopically fitted, and adapted to be able to adjust a separation distance between the fourth diaphragm 34 and the imaging device C. This enables the intensity profile with respect to the tilt variations to be further precisely optimized.

The reason for, in the case of using the lighting device for inspection 100 configured as described above, making it easy to detect a very small defect or the like as contrast in the imaging device C is described with reference to FIGS. 5(a) and 5(b). Note that irradiation solid angles indicated by dashed lines in FIGS. 5(a) and 5(b) are ones in a conventional example where the first diaphragm 31 is not present and an irradiation solid angle cannot be adjusted, whereas irradiation solid angles indicated by solid lines are ones in an example where an irradiation solid angle is decreased in the lighting device for inspection 100 of the present embodiment.

As illustrated in FIG. 5(a), in the case where no defect is present on the inspection object W, inspection light and reflected light appear as, for example, symmetrical mirror images based on specular reflection. As illustrated in FIG. 5(b), in the case where a defect or the like is present on the inspection object W, a reflection direction of reflected light is slightly changed. In this case, if the defect is very small, a change in direction of the reflected light is also small, so that irradiating the inspection light at the irradiation solid angle indicated by the dashed lines in the conventional example correspondingly increases a solid angle of the reflected light as well, and therefore the reflected light does not deviate from an observation solid angle C1 of the imaging device C. On the other hand, in the present embodiment, by decreasing the irradiation solid angle with the first diaphragm 31, the solid angle of the reflected light is also decreased, so that even in the case where a tilt of the reflected light is slightly changed, the observation solid angle C1 of the imaging device C is arranged outside the solid angle of the reflected light, and therefore the defect is imaged darkly. As described, the irradiation solid angle and the solid angle of the reflected light can be appropriately set with the first diaphragm 31, and therefore a defect or the like, which could not have been detected previously, can be captured as contrast through machine vision. Also, an intensity variation in observation light due to a tilt variation of the reflected light can be precisely optimized.

Regarding the intensity variation, as described above, a variation width, variation start point, variation end point, variation level, and the like thereof are determined by respective magnitudes of the solid angle of the reflected light reflected from the object and the observation solid angle, and an inclusion relation between the solid angles. The solid angle of the reflected light can be controlled by the solid angle of the irradiation light, and therefore using the present invention that can uniformly control solid angles of reflected light within a visual field range enables a desired intensity profile to be obtained for feature points on an object surface, such as defects.

Note that, in this case, by controlling tilts of central axes of the solid angles of the reflected light appropriately for changes in tilts of central axes of corresponding observation solid angles within the visual field range in order to uniformly keep an inclusion relation between the solid angles of the reflected light and the corresponding observation solid angles within the visual field range, uniform intensity variations can be obtained for the feature points such as defects.

The tilts of the central axes of the solid angles of the reflected light within the visual field range can be optimally controlled by appropriately selecting a position of the first diaphragm 31 on the light axis.

Variations of the first embodiment are described. In the following description, members corresponding to those in the above-described embodiment are denoted by the same reference signs.

Figure 6:
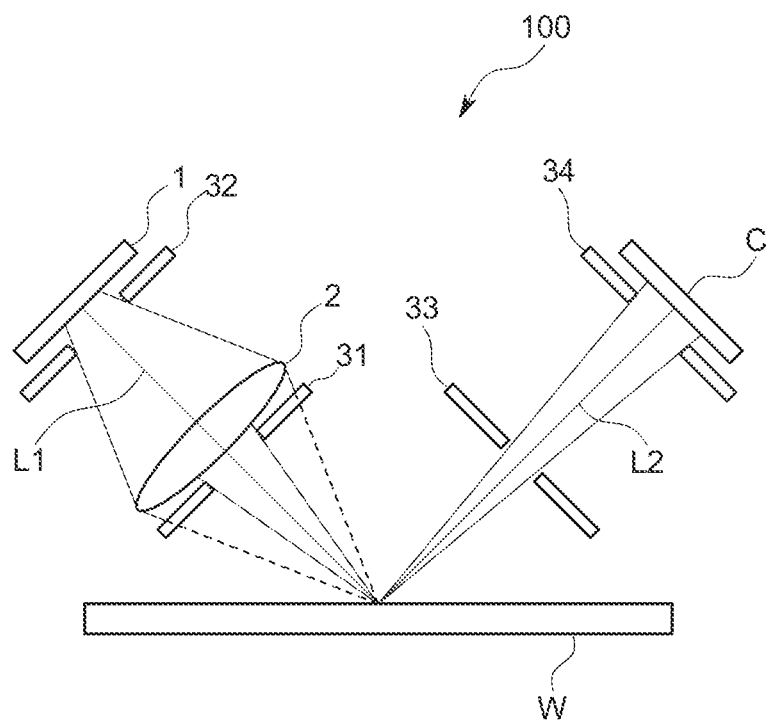
FIG. 6 is a schematic diagram illustrating an example of a lighting device for inspection in a variation of the first embodiment of the present invention.

In the above-described embodiment, the lighting device for inspection is configured as the coaxial lighting device; however, as illustrated in FIG. 6, the irradiation light path L1 and the reflection light path L2 may be independently configured so as not to have the overlap part. In short, it is only necessary that the lighting device for inspection is adapted to be able to condense the inspection light emitted from the surface light source 1 with the lens 2 of which a focal point is set on the inspection object W, and also adjust irradiation solid angles of the inspection light with the first diaphragm 31 provided near the lens 2. In addition, the lighting device for inspection may be adapted to use the second, third, and fourth diaphragms 32, 33, and 34 as necessary.

Also, the focal position of the lens is not limited to a position on the surface of the inspection object, but may be displaced slightly forward or backward from the surface as long as the position is near the surface. In addition, the inspection object and the feature point such as a defect are not limited to specific ones, and the lighting device for inspection of the present invention can be used for various purposes.

Next, a second embodiment is described. Members corresponding to respective members in the first embodiment are denoted by the same signs.

Figure 7:
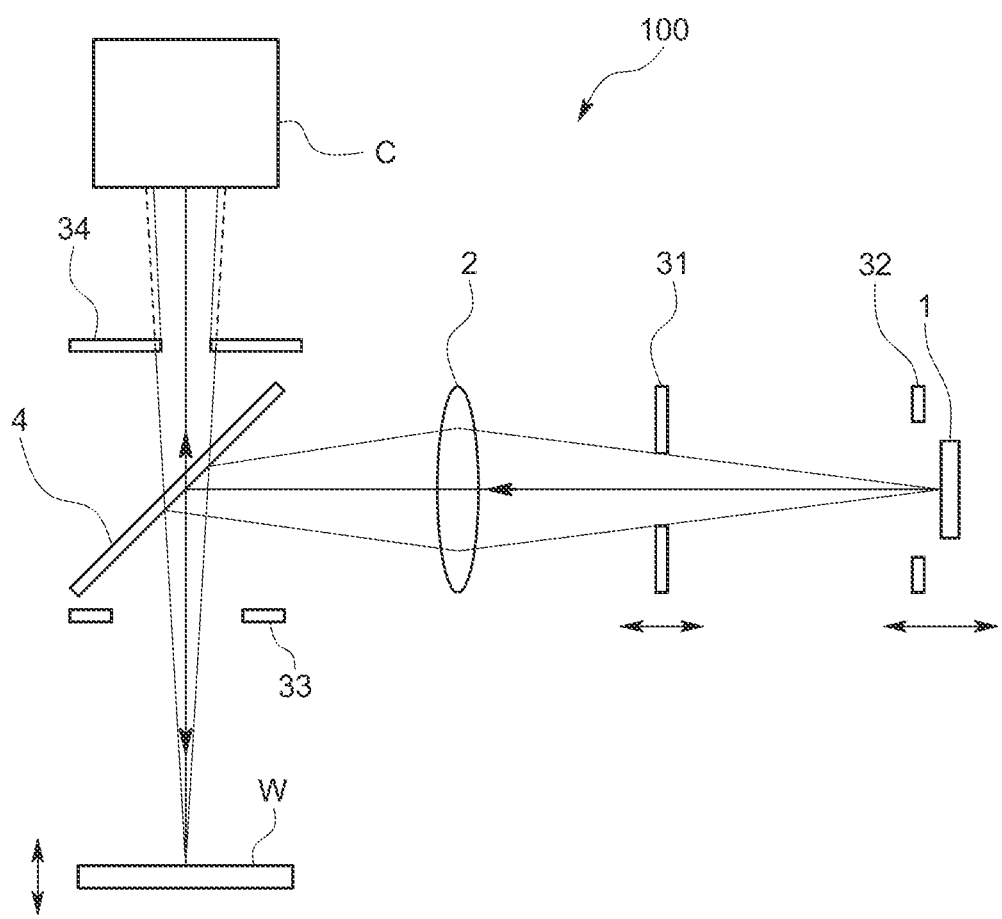
FIG. 7 is a schematic diagram illustrating a simplified light path in a lighting device for inspection in a second embodiment of the present invention.

A lighting device for inspection 100 of the second embodiment is, as illustrated in a simplified light path diagram of FIG. 7, different from the first embodiment in that a first diaphragm 31 is positioned between a surface light source 1 and a lens 2, and that the position of the first diaphragm 31 is variably set.

Details of respective parts are described. In drawings used for the following description, mainly, only an irradiation optical system is described, and for easy understandings, a light path bent by a half mirror 4 is also illustrated with being converted to a linear light path.

Figure 8A:
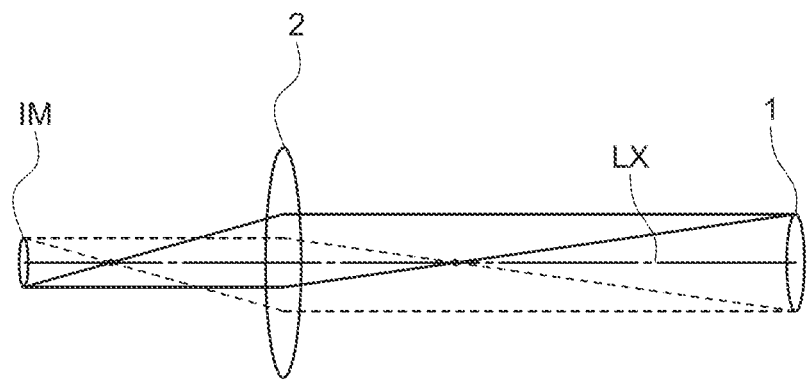
FIGS. 8(a) and 8(b) are schematic diagrams illustrating an imaging state and a change based on arrangement of a first diaphragm in the lighting device for inspection in the second embodiment.
Figure 8B:
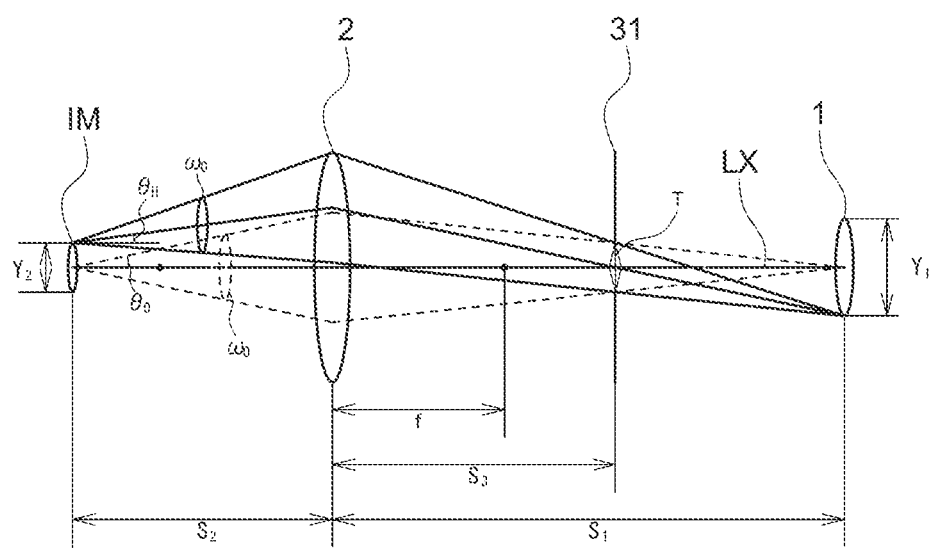
Figure 9:
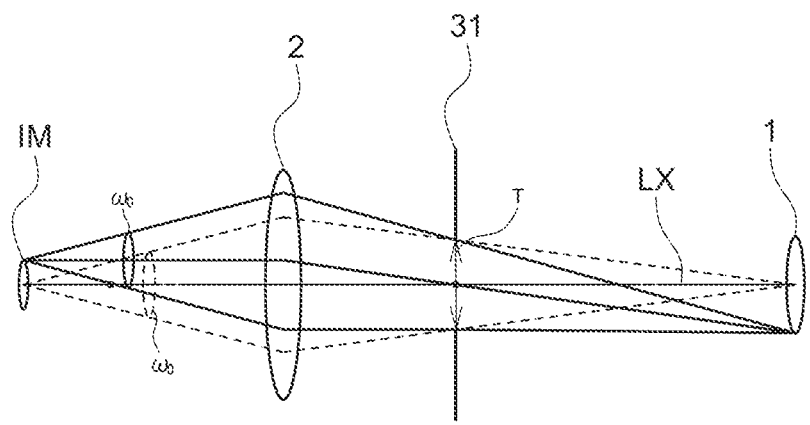
FIGS. 9(a) and 9(b) are schematic diagrams illustrating that by changing an opening diameter of the first diaphragm of the lighting device for inspection in the second embodiment, the magnitude of an irradiation solid angle is changed, but the size of an image plane is not changed.
Figure 9:
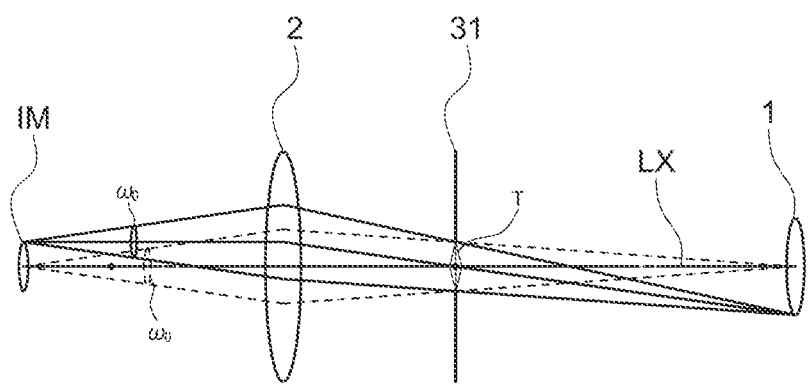

As illustrated in FIG. 8(a) in which the first diaphragm 31 is omitted, positions of the surface light source 1 and the lens 2 with respect to an inspection object W are set such that an image plane IM on which the surface light source 1 is imaged is present on the inspection object W. In addition, as illustrated in FIG. 8(b) in which the first diaphragm 31 is inclusively illustrated, the lighting device for inspection is configured to be able to adjust the magnitude of an irradiation solid angle $\omega_o$ on the image plane IM and a tilt of the central axis of the irradiation solid angle $\omega_o$ with respect to a light axis LX by changing the position of the first diaphragm 31 with respect to the lens 2, and an opening diameter T of the first diaphragm 31. That is, as illustrated in FIGS. 9(a) and 9(b), as the opening diameter T of the first diaphragm 31 is decreased, irradiation solid angles $\omega_o$ at respective points on the image plane IM can be decreased. Further, as illustrated in FIGS. 9(a) and 9(b), it turns out that even in the case of changing the opening diameter T of the first diaphragm 31, the size of the image plane IM does not change. Accordingly, such a configuration enables the magnitudes of the irradiation solid angles $\omega_o$ at respective points to be uniformly freely adjusted without changing a range of inspection light irradiated onto the inspection object W. Further, in the case where the opening diameter T can be decreased, solid angles of reflected light from the inspection object W can also be decreased, and therefore if a tilt of the central axis of a reflection solid angle is changed by a very small defect or flaw, the reflection solid angle does not meet an inclusion relation set with a corresponding observation solid angle of an imaging device. Accordingly, even a feature point such as a very small defect can be easily detected as contrast as described in the first embodiment.

In addition, it is also possible that in the case where an irradiation solid angle is larger than a corresponding observation solid angle, intensity does not change as long as a level of a feature point such as a defect is within a certain range, and if the level exceeds the certain range, contrast is made to appear.

As described, by adjusting the respective magnitudes of an irradiation solid angle and a corresponding observation solid angle, and an inclusion relation between them, an image intensity profile to be obtained correspondingly to feature points such as defects can be freely set.

That is, in addition to enabling a certain detection threshold value for a feature point such as a defect to be set so as to prevent intensity from being changed up to the threshold value and change the intensity upon exceeding the threshold value, depending on how a profile result comes out, a change in intensity after exceeding the threshold value can be slowly made or abruptly made, or only in a specific direction, the change in intensity can also be made sensitive, and therefore an intensity profile of a gray scale image, which is obtained for various feature points, can be optimized.

Next, the adjustment of tilt states of irradiation solid angles $\omega_o$ at respective points on an image plane IM is described. The lighting device for inspection 100 of the second embodiment is adapted to be able to change the setting position $S_3$ of the first diaphragm 31 so as to optimize an irradiation state of the inspection light appropriately for the shape of the inspection object W or a configuration of an imaging device C. That is, the position of the first diaphragm 31 with respect to the lens 2 is set such that the central axis of an irradiation solid angle $\omega_o$ determined by a part of the inspection light, which is incident on an outer edge part of the image plane IM, is parallel to the light axis LX, or is displaced from the light axis and tilted by a predetermined amount.

More specifically, a tilt state of the central axis of the irradiation solid angle $\omega_o$ can be changed to any of three states depending on the position of the first diaphragm 31 with respect to a focal point of the lens 2. As illustrated in FIG. 10(a), in the case of desiring to tilt the central axis of the irradiation solid angle $\omega_o$ from the outer edge side toward the center side of the image plane IM, the first diaphragm 31 is arranged outside the focal point of the lens 2. Also, as illustrated in FIG. 10(b), in the case of desiring to tilt the central axis of the irradiation solid angle $\omega_o$ from the center side toward the outer edge side of the image plane IM, the first diaphragm 31 is arranged inside the focal point of the lens 2. Further, as illustrated in FIG. 10(c), in the case of desiring to make the central axis of the irradiation solid angle $\omega_o$ parallel to the light axis LX, the first diaphragm 31 is arranged at the focal point of the lens 2.

Tendencies of displacement and tilt of the central axis of the irradiation solid angle $\omega_o$ with respect to the light axis LX in each of the setting conditions are described in detail with reference to FIG. 11. On the left side of FIG. 11, enlarged diagrams near the image plane IM are illustrated, whereas on the right side, schematic diagrams each illustrating a directional distribution of the central axes of irradiation solid angles $\omega_o$ are illustrated.

In the case where, as illustrated in FIG. 10(a), the first diaphragm 31 is arranged outside the focal point of the lens 2, as illustrated in FIG. 11(a), except for the center of the image plane IM, the central axes of the irradiation solid angles $\omega_o$ are tilted from the outer edge side toward the center side of the image plane IM, and an outer central axis has a larger tilt. In the case where, as illustrated in FIG. 10(b), the first diaphragm 31 is arranged inside the lens 2, as illustrated in FIG. 11(b), except for the center of the image plane IM, the central axes of the irradiation solid angles $\omega_o$ are tilted from the center side toward the outer edge side of the image plane IM, and an outer central axis has a larger tilt. In the case where, as illustrated in FIG. 10(c), the first diaphragm 31 is arranged at the focal point of the lens 2, as illustrated in FIG. 11(c), at all points on the image plane IM, the central axes of the irradiation solid angles $\omega_o$ are parallel to the light axis LX.

Next, an example of a way to utilize the tilt distribution characteristic of an irradiation solid angle $\omega_o$, which is different depending on the position of the first diaphragm 31, for inspection is described.

For example, consider the case of desiring to increase defect detection accuracy by making the reflected light of the inspection light irradiated onto the inspection object W entirely return as parallel light. That is, as illustrated in FIG. 12(a), in the case where the inspection object W has a convex surface, by positioning the first diaphragm 31 outside the focal point of the lens 2, all the central axes of solid angles of the reflected light can be made parallel to the light axis LX. Similarly, as illustrated in FIG. 12(b), in the case where the inspection object W has a concave surface, by arranging the position of the first diaphragm 31 inside the focal point of the lens 2, the reflected light from the concave surface can be formed as parallel light. Further, as illustrated in FIG. 12(c), in the case where the inspection object W has a flat surface, it is only necessary to set the position of the first diaphragm 31 at the focal point of the lens 2.

As described, states of irradiation solid angles $\omega_o$, which are suitable for the shape of the inspection object W, can be created on the basis of the position of the first diaphragm 31. In addition, even in the case of adjusting the irradiation solid angles $\omega_o$, an irradiation range of the inspection light is not affected at all, and the inspection light can be successively irradiated onto the same area.

In the case of desiring to more strictly adjust tilt states of the central axes of the irradiation solid angles $\omega_o$, i.e., angles formed between the central axes of the irradiation solid angles $\omega_o$ and the light axis LX appropriately for the shape or the like of the inspection object W, it is only necessary to set the position of the first diaphragm 31 on the basis of desired setting angles $\theta_H$ formed between the central axes of the irradiation solid angles $\omega_o$ and the light axis LX, and a magnification ratio M on the image plane IM on which the surface light source 1 is imaged through the lens 2.

This is described with reference to drawings such as FIGS. 13(a) and 14(b).

First, given that a distance from the surface light source 1 to the center of the lens 2 is $S_1$, and a distance from the center of the lens 2 to the image plane IM is $S_2$, $S_1$ and $S_2$ meet Expression 1 below based on the Gaussian formulas using a focal length f.

$$1/S_1 + 1/S_2 = 1/f \qquad \text{Expression 1}$$

Also, given that a magnification ratio of a diameter $Y_2$ of the image plane IM to a diameter $Y_1$ of the surface light source 1 is M, Expression 2 holds.

$$M = S_1/S_2 \qquad \text{Expression 2}$$

That is, $S_1$ and $S_2$ can be determined according to imaging conditions and a desired irradiation range on the inspection object W. For example, in the case where the diameter $Y_1$ of the surface light source 1 is predetermined, the diameter $Y_2$ of the image plane IM is determined from the desired irradiation range, and the magnification ratio M is also determined. Accordingly, $S_1$ and $S_2$ can be determined from the irradiation range on the basis of Expressions 1 and 2. Next, how to determine the tilt states of the irradiation solid angles $\omega_o$ is described.

Figure 13A:
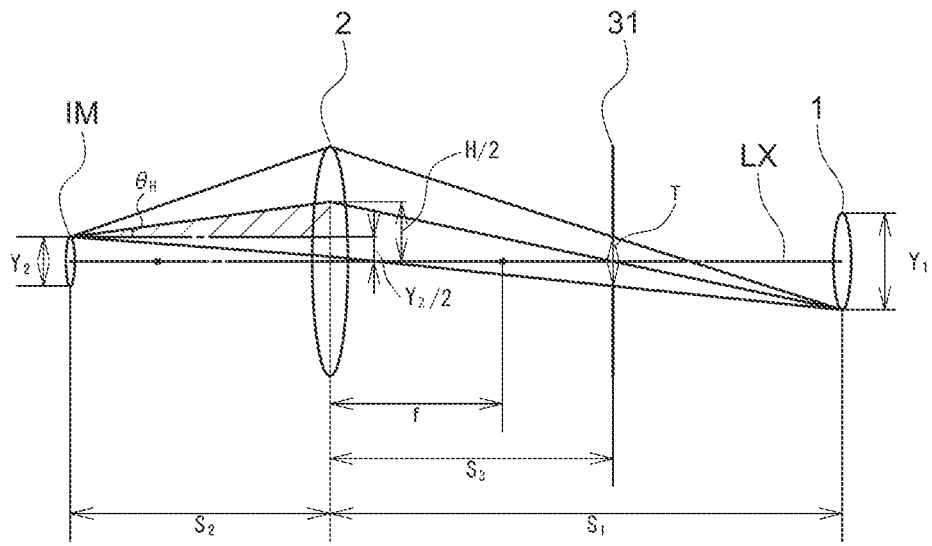
FIGS. 13(a) and 13(b) are schematic diagrams for explaining relationships between a tilt of the central axis of an irradiation solid angle and various parameters of the lighting device for inspection in the second embodiment.

As illustrated in FIG. 13(a), for an angle $\theta_H$ formed between the central axis of an irradiation solid angle $\omega_o$ at an outer edge part of the image plane IM and the light axis LX, a relational expression as given by Expression 3 holds on the basis of a triangular shape indicated as a shaded part:

$$\tan \theta_H = (H/2 - Y_2/2)S_2 = (H - Y_2)/2S_2 \qquad \text{Expression 3}$$

where $\theta_H$ is the angle formed between the central axis of the irradiation solid angle $\omega_o$ and the light axis LX, and $\theta_H$ is set negative in the case where the central axis intersects with the light axis LX from the outer edge side toward the center side, whereas in the case where the central axis intersects with the light axis LX from the center side toward the outer edge side, $\theta_H$ is set positive. In addition, $Y_2$: the diameter of the image plane IM, H/2: a distance from the center of the lens 2 to a position where a principal ray of the inspection light reaching the outermost edge of the image plane IM passes, and $S_2$: the distance from the center of the lens 2 to the image plane IM.

Figure 13B:
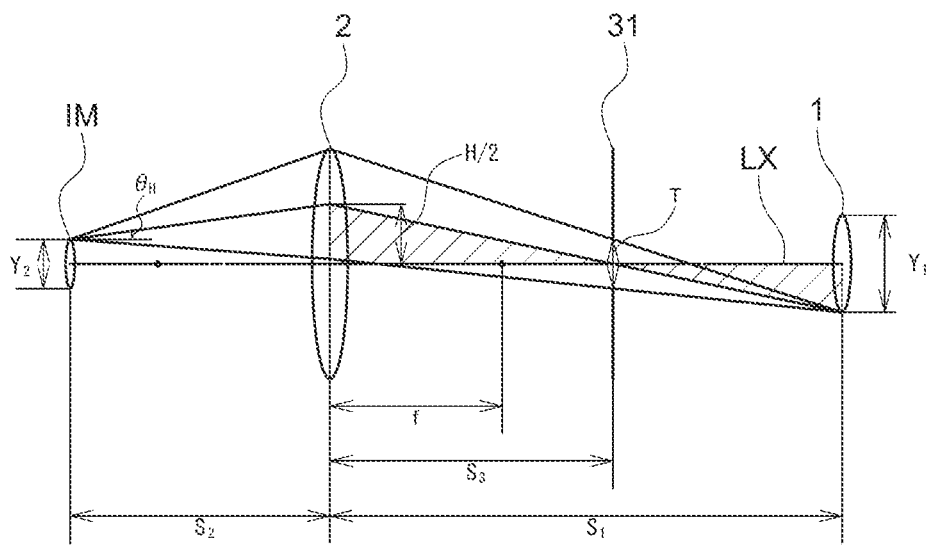

Also, two triangular shapes indicated by oblique lines in FIG. 13(b) are similar, and therefore H can be given as Expression 4.

$$H = S_3 Y_1 / (S_1 - S_3) \qquad \text{Expression 4}$$

Here, $S_1$: the distance between the surface light source 1 and the center of the lens 2, $S_3$: the distance between the first diaphragm 31 and the center of the lens 2, and $Y_1$: the diameter of the surface light source 1.

Further, given that the magnification ratio that is a ratio in size of the image plane IM to the surface light source 1 is M, Expression 3 can be described using Expression 4 as Expression 5.

$$\tan \theta_H = (S_3 Y_1 / (S_1 - S_3) - MY_1)/2S_2 \qquad \text{Expression 5}$$

$Y_1$ has a value determined by the size of a surface light source 1 to be used because it is the diameter of the surface light source 1, and as described above, $S_1$ and $S_2$ can be determined from a desired magnification ratio M and the focal length f, so that on the basis of a desired setting tilt angle $\theta_H$ and a desired setting magnification ratio M, $S_3$ that is the position of the first diaphragm 31 can be determined from Expression (5).

Finally, how to adjust the magnitudes of the irradiation solid angles $\omega_o$ is described.

Figure 14A:
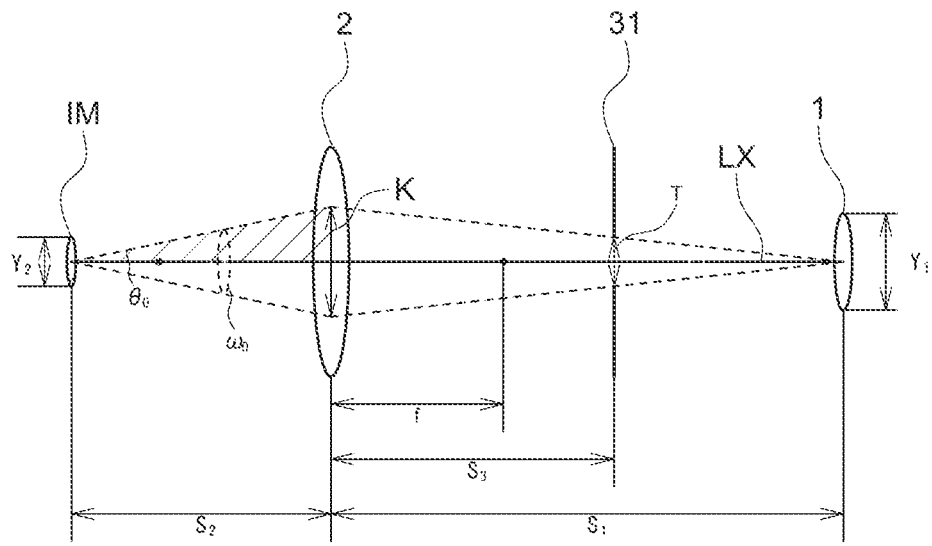
FIGS. 14(a) and 14(b) are schematic diagrams for explaining relationships between the magnitude of an irradiation solid angle and various parameters of the lighting device for inspection in the second embodiment.

Given that a planar half angle of an irradiation solid angle $\omega_o$ of the inspection light incident on the image plane IM is $\theta_o$, and a diameter of the inspection light incident on the lens 2 through the first diaphragm 31 is K, a relational expression as given by Expression 6 can be derived from a triangular shape indicated as a shaded part in FIG. 14(a).

$$\tan \theta_o = (K/2)/S_2 \, \theta_o = \tan^{-1}(K/2S_2) \qquad \text{Expression 6}$$

Figure 14B:
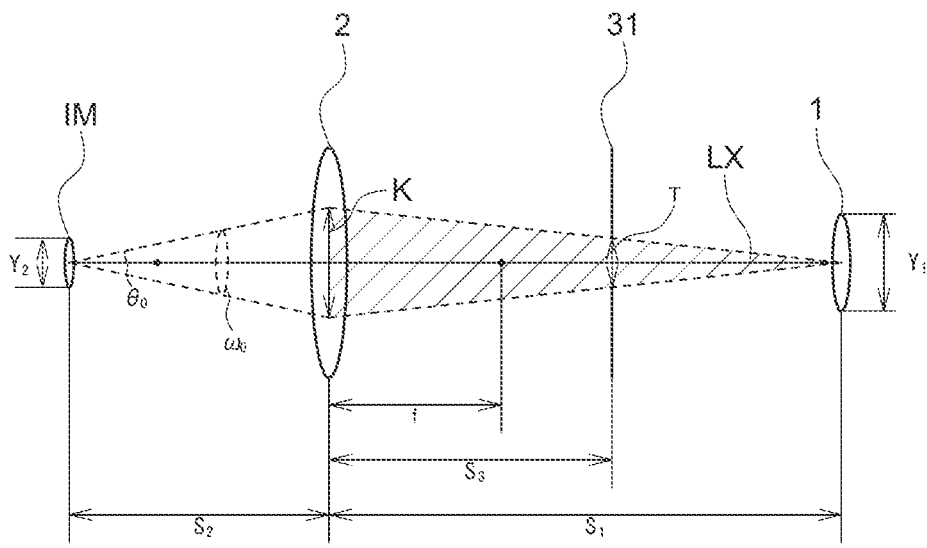

Also, given that the opening diameter of the first diaphragm 31 is T, K can be given as Expression 7 on the basis of two similar triangular shapes indicated as shaded parts in FIG. 14(b).

$$K = S_1 T/(S_1-S_3) \qquad \text{Expression 7}$$

In addition, the irradiation solid angle $\omega_o$ can be described using the planar half angle $\theta_o$ of the irradiation solid angle $\omega_o$ as Expression 8.

$$\omega_o = 2\pi(1-\cos\theta_o) \qquad \text{Expression 8}$$

Accordingly, from Expressions 6, 7, and 8, the irradiation solid angle $\omega_o$ can be given as Expression 9.

$$\omega_o = 2\pi[1-\cos\{\tan^{-1}(S_1T/2S_2(S_1-S_3))\}] \qquad \text{Expression 9}$$

That is, as given by Expression 9, it turns out that the irradiation solid angle $\omega_o$ can be determined by the opening diameter T of the first diaphragm 31 and the setup position $S_3$ of the first diaphragm 31. In addition, in the case of setting the position $S_3$ of the first diaphragm 31 in order to set the tilt angle $\theta_H$ of the central axis of the irradiation solid angle $\omega_o$ to a predetermined angle in advance, only by changing the opening diameter T of the first diaphragm 31, only the magnitude of the irradiation solid angle $\omega_o$ can be independently set to a desired value.

From the above, an adjusting method suitable for respectively independently adjusting the irradiation range of the inspection light on the inspection object W, the tilt states of the irradiation solid angles $\omega_o$ on the outer edge and entire area of the irradiation range, and the magnitudes of the irradiation solid angles $\omega_o$ in the lighting device for inspection 100 of this embodiment is as follows.

First, on the basis of the size of the surface light source 1 used, and the size of the image plane IM corresponding to a desired irradiation range of the inspection light, the magnification ratio M is set. Then, on the basis of the magnification ratio M, and the focal length f of the lens 2 used, the separation distance $S_1$ between the surface light source 1 and the lens 2, and the separation distance $S_2$ between the lens 2 and the inspection object W are set.

Subsequently, the position $S_3$ of the first diaphragm 31 is set so as to achieve the tilt distribution and tilt states of the irradiation solid angles $\omega_o$, which are appropriate for inspection, depending on whether the surface of the inspection target W is any of convex, concave, and flat surfaces, for example. That is, in the case of the concave surface, the first diaphragm 31 is arranged inside the focal point; in the case of the concave surface, the first diaphragm 31 is arranged outside the focal point; and in the case of the flat surface, the first diaphragm 31 is arranged at the focal point. The strict tilt states are only required to be set on the basis of Expression 5.

Finally, the irradiation solid angles $\omega_o$ are adjusted with $S_1$, $S_2$, and $\theta_H$ being fixed. For this purpose, the opening diameter T of the first diaphragm 31 is set on the basis of desired irradiation solid angles $\omega_o$.

As described, according to the lighting device for inspection 100 of the second embodiment, without changing the size of the image plane IM corresponding to the irradiation range, only the tilt distribution and tilt states of the irradiation solid angles $\omega_o$, and only the magnitudes of the irradiation solid angles $\omega_o$ can be respectively independently adjusted by adjusting the position $S_3$ of the first diaphragm 31 and by adjusting the opening diameter T.

Accordingly, without wasting the inspection light from the surface light source 1, the irradiation range can be limited to a predetermined range to reduce stray light, and also the states of the irradiation solid angles $\omega_o$ appropriate for the surface shape of the inspection object W or characteristics of an observation optical system can be achieved to detect even a feature point such as a very small defect.

Variations of the second embodiment are described.

In the second embodiment, the size of the surface light source, and the focal length of the lens are treated as predetermined values, respectively; however, such values may be appropriately changed depending on an inspection object. For example, the size of the surface light source can also be decreased by adjusting an opening diameter of a second diaphragm provided near the surface light source. Also, the present invention may be adapted to be able to appropriately select a lens having a different focal length or a different numerical aperture.

From the theoretical formulas shown in the second embodiment, it seems that by adjusting the respective values, the size of the image plane, the irradiation solid angles, and the tilt of the irradiation solid angle at the outer edge part of the image plane can be respectively changed from zero to infinity, zero to $2\pi$, and 0 to $\pm 90$ degrees; however, in order to converge the size of the lens, and the separation distances between the respective members to realistic values, respectively, it is only necessary that for the size of the image plane, the magnitudes of the irradiation solid angles, and the tilts of the central axes of the irradiation solid angles, values up to approximately 10 m in diameter, up to 70 degrees in planar half angle, and up to approximately $\pm 70$ degrees are used as setting values, respectively.

Furthermore, the various variations and embodiments may be combined unless contrary to the scope of the present invention.

INDUSTRIAL APPLICABILITY

According to the present invention, most of the emitted inspection light can be made to reach the inspection object, and also tilt states of the central axes of and the magnitudes of irradiation solid angles of the inspection light at respective points on the inspection object can be adjusted, so that a lighting device for inspection and lighting method for inspection that enables inspection appropriate for the shape and characteristics of an inspection target can be provided.

The invention claimed is:
1. A lighting device for inspection, comprising:
  a surface light source that emits inspection light;
  a lens that is provided on a light axis of the inspection light emitted from the surface light source, the lens being a closest lens to the inspection object, and between an inspection object and the surface light source; and
  a first diaphragm that is provided between the surface light source and the lens, or between the lens and the inspection object, wherein
  positions of the surface light source and the lens with respect to the inspection object are set such that an image plane on which the surface light source is imaged in focus is present near the inspection object,
  a position of the first diaphragm with respect to the lens is set such that a central axis of an irradiation solid angle determined by the inspection light, which is incident on an outer edge part of the image plane, is parallel to the light axis, or is displaced from the light axis and tilted by a predetermined amount, and
  the inspection object has a convex inspection surface, the first diaphragm is arranged outside a focal point of the lens such that the central axis of the irradiation solid angle is tilted from an outer edge side toward a center side of the image plane.

2. A lighting device for inspection, comprising:

a surface light source that emits inspection light;

a lens that is provided on a light axis of the inspection light emitted from the surface light source, the lens being a closest lens to the inspection object, and between an inspection object and the surface light source; and a first diaphragm that is provided between the surface light source and the lens, or between the lens and the inspection object, wherein positions of the surface light source and the lens with respect to the inspection object are set such that an image plane on which the surface light source is imaged in focus is present near the inspection object, a position of the first diaphragm with respect to the lens is set such that a central axis of an irradiation solid angle determined by the inspection light, which is incident on an outer edge part of the image plane, is parallel to the light axis, or is displaced from the light axis and tilted by a predetermined amount, and the inspection object has a concave inspection surface, the first diaphragm is arranged inside a focal point of the lens such that the central axis of the irradiation solid angle is tilted from a center side toward an outer edge side of the image plane.

3. A lighting method for inspection, the method being used for a lighting device for inspection, the device comprising: a surface light source that emits inspection light; a lens that is provided on a light axis of the inspection light emitted from the surface light source, and between an inspection object and the surface light source, the lens being a closest lens to the inspection object; and a first diaphragm that is provided between the surface light source and the lens, or between the lens and the inspection object, the method comprising:

an imaging position setting step of setting positions of the surface light source and the lens with respect to the inspection object such that an image plane on which the surface light source is imaged in focus is present near the inspection object; and an irradiation solid angle tilt adjusting step of setting a position of the first diaphragm with respect to the lens such that a central axis of an irradiation solid angle determined by a part of the inspection light which is incident on an outer edge part of the image plane is parallel to the light axis, or is displaced from the light axis and tilted by a predetermined amount, wherein the inspection object has a convex inspection surface, the first diaphragm is arranged outside a focal point of the lens such that the central axis of the irradiation solid angle is tilted from an outer edge side toward a center side of the image plane.

4. A lighting method for inspection, the method being used for a lighting device for inspection, the device comprising: a surface light source that emits inspection light; a lens that is provided on a light axis of the inspection light emitted from the surface light source, and between an inspection object and the surface light source, the lens being a closest lens to the inspection object; and a first diaphragm that is provided between the surface light source and the lens, or between the lens and the inspection object, the method comprising:

an imaging position setting step of setting positions of the surface light source and the lens with respect to the inspection object such that an image plane on which the surface light source is imaged in focus is present near the inspection object; and an irradiation solid angle tilt adjusting step of setting a position of the first diaphragm with respect to the lens such that a central axis of an irradiation solid angle determined by a part of the inspection light which is incident on an outer edge part of the image plane is parallel to the light axis, or is displaced from the light axis and tilted by a predetermined amount, wherein the inspection object has a concave inspection surface, the first diaphragm is arranged inside a focal point of the lens such that the central axis of the irradiation solid angle is tilted from a center side toward an outer edge side of the image plane.

* * * * *